United States Patent [19]

Schou et al.

[11] Patent Number: 5,866,392
[45] Date of Patent: Feb. 2, 1999

[54] CELLOBIOSE OXIDASE, AND ENZYMATIC AGENT AND A PROCESS FOR TREATING PAPER PULP

[75] Inventors: Charlotte Schou, Frederiksberg; Martin Schülein, Copenhagen; Thomas Vollmond, Søborg, all of Denmark

[73] Assignee: Novo Nordisk A/S, Bagsvaerd, Denmark

[21] Appl. No.: 672,006

[22] Filed: Jun. 24, 1996

Related U.S. Application Data

[62] Division of Ser. No. 356,274, filed as PCT/DK93/00221, Jul. 2, 1993, published as WO94/01538, Jan. 20, 1994, abandoned.

[30] Foreign Application Priority Data

Jul. 3, 1992 [DK] Denmark .................................. 08752/92

[51] Int. Cl.⁶ .................................. C12N 9/04; C12N 9/02
[52] U.S. Cl. ............................ 435/190; 435/189; 435/911
[58] Field of Search ...................................... 435/190, 189, 435/911

[56] References Cited

PUBLICATIONS

Coudray et al, Biochem. J. 203:277–284 (1982).
Morpeth et al, Biochem J. 228:557–564 (1985).
Ayers et al, Methods Enzymol. 89: 129–135 (1982).

*Primary Examiner*—Francisco C. Prats
*Attorney, Agent, or Firm*—Steve T. Zelson, Esq.; Valeta A. Gregg, Esq.

[57] ABSTRACT

Enzyme exhibiting cellobiose oxidase activity, which enzyme has a relative activity of at least 70% at a pH of about 9 and a temperature of about 50° C. An enzymatic agent comprising cellobiose oxidase and an endoglycanase and/or oxidoreductase. A process of bleaching paper pulp using cellobiose oxidase.

7 Claims, 2 Drawing Sheets ial application of application Ser. No. 08/356,274, filed Dec. 15, 1994, now abandoned, the contents of which are incorporated herein by reference in their entirety and which is a National Stage of PCT/DK93/00221, filed Jul. 2, 1993 published as WO94/01538, Jan. 20, 1994.

CELLOBIOSE OXIDASE, AND ENZYMATIC AGENT AND A PROCESS FOR TREATING PAPER PULP

This is a divisional application of application Ser. No. 08/356,274, filed Dec. 15, 1994, now abandoned, the contents of which are incorporated herein by reference in their entirety and which is a National Stage of PCT/DK93/00221, filed Jul. 2, 1993 published as WO94/01538, Jan. 20, 1994.

FIELD OF INVENTION

The present invention relates to a novel cellobiose oxidase, an enzymatic agent comprising the cellobiose oxidase and a process of bleaching paper pulp using the cellobiose oxidase.

BACKGROUND OF THE INVENTION

Chemical pulping (known as Kraft pulping) of wood chips for paper production involves alkaline sulphate cooking of the wood chips to remove 90–98% of the lignin present in the wood. The remaining 2–10% lignin imparts a dark brown colour to the pulp which tends to darken in UV light or by oxidation. To obtain a white pulp, the lignin present in the pulp must therefore be removed by a variety of bleaching procedures, most of which involve treatment with chlorine or chlorine dioxide, ozone, oxygen or hydrogen peroxide.

Due to an increasing concern about the environmental impact of the chemicals generated in the bleaching process, enzymatic treatment of the pulp has been proposed with a view to removing lignin from paper pulp while reducing the amount of bleaching chemicals needed in the process, vide e.g. "The third International Conference on Biotechnology in the Pulp and Paper industry", Stockholm, 16–19 Jun., 1986, pp. 67–69.

The enzymatic treatment of paper pulp hitherto described has mostly been carried out at an acid pH with hemicellulases with an acid pH optimum, vide e.g. "4th International symposium of Wood and Pulping Chemistry", Paris, 22–30 Apr., 1987, Vol. 1, pp. 151–154, or with a fungal preparation from Trichoderma, cf. M. G. Paice and L. Jurasek, *J. Wood Chem. Technol.* 4, 1989, pp. 187–198; or D. J. Senior et al., *Biotechnol. Lett.* 10, 1988, pp. 907–912, requiring a pH adjustment of the wood pulp to below a pH of 6.

Xylanase compositions are also used in the pulp and paper industry in the pulp bleaching process to enhance the brightness of bleached pulps, decrease the amount of chemicals used for bleaching as well as in the bleaching of recycled paper, cf. K. E. L. Eriksson, *Wood Science and Technology* 24, 1990, pp. 79–101, M. G. Paice et al., *Biotechnol. and Bioeng.* 32, 1988, pp. 235–239, J. C. Pommier et al., *Tappi Journal,* 1989, pp. 187–191. The use of an alkaline xylanase for pulp treatment is described in WO 91/02839.

In wood, lignin is linked to xylan. Xylanase is capable of catalysing the hydrolysis of the xylan so that an increased release of lignin occurs during bleaching. Another enzyme, cellobiose oxidase, has been found to be important for lignin degradation in that it reduces phenoxy radicals and guinones formed by the action of phenol oxidases on degradation products from lignin, thereby oxidising cellobiose and higher cellodextrins to the corresponding lactones. A cellobiose oxidase from *Phanerochaete chrysosporium* has been described in A. R. Ayers et al.,*Eur. J. Biochem.* 90, 1978, pp. 171–181, and further characterized by F. F. Morpeth, *Biochem. J.* 228, 1985, pp. 557–564. This cellobiose oxidase was found to have a pH optimum at pH 5. Cellobiose oxidases have also been found in brown rot fungus *Coniophora puteana* (D. R. Schmidhalter and G. Canevascini, *Appl. Microbiol. Biotechnol.* 37, 1992, pp. 431–436) and soft rot fungi such as Monilia sp. (R. F. H. Dekker, *J. Gen. Microbiol.* 120, 1980, pp. 309–316), *Chaetomium cellulolyticum* (P. Fähnrich and K. Irrgang, *Biotechnol. Lett.* 4(12), 1982, pp. 775–780), *Myceliophthora (Sporotrichum) thermophile* (M.-R. Coudray et al., *Biochem. J.* 203, 1982, pp. 277–284) and *Sclerotium rolfsii* (J. C. Sadana and R. V. Patil, *J. Gen. Microbiol.* 131, 1985, pp. 1917–1923). It is believed that these cellobiose oxidases participate in cellulose degradation.

DESCRIPTION OF THE INVENTION

Figure 1:
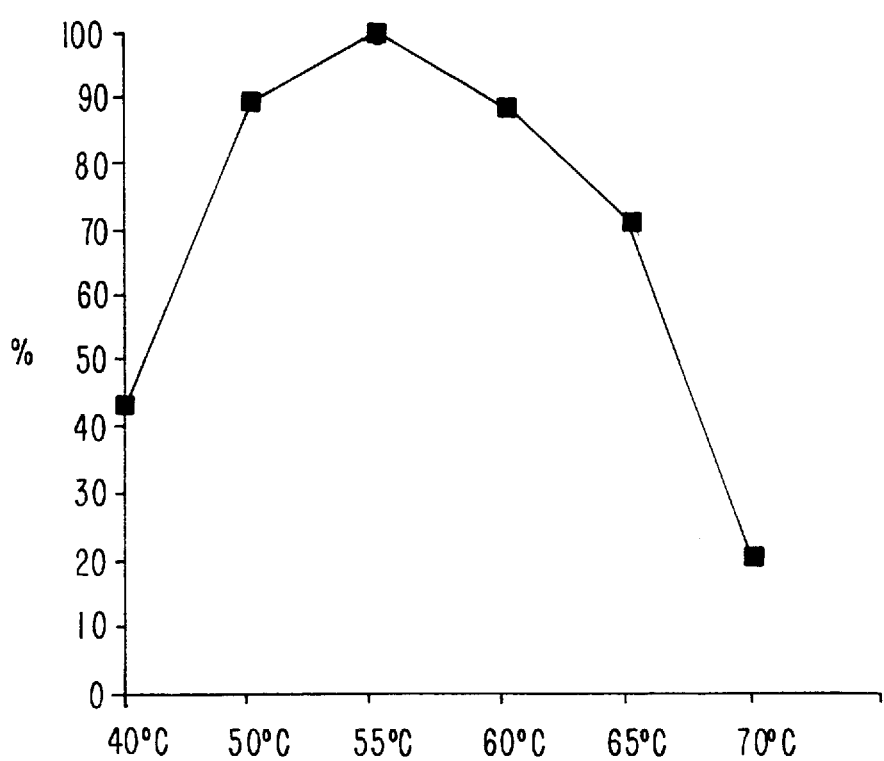
FIG. 1 is a plot of relative activity of the cellobiose oxidase enzyme versus temperature.

An object of the invention is to provide a cellobiose oxidase which may be used in a pulp bleaching process under alkaline conditions.

Accordingly, the present invention relates to an enzyme exhibiting cellobiose oxidase activity, which enzyme has a relative activity of at least 70% at a pH of about 9 and a temperature of about 50° C.

In the present context, the term "cellobiose oxidase" is intended to indicate a hemoflavoprotein enzyme which is capable of oxidising cellobiose and cellodextrins to the corresponding lactones using oxygen, Fe(III)-containing compounds, such as ferric cyanide, or various aromatic compunds as the electron acceptor. The term "relative activity" is intended to be understood in terms of the ability of the enzyme to oxidise cellobiose in the presence of such electron acceptors relative to the maximum activity.

A cellobiose oxidase of th is type is one which is immunologically reactive with an antibody raised against a cellobiose oxidase derived from a strain of Humicola. The term "immunologically reactive" is intended to indicate an enzyme which has at least one epitope in common with the cellobiose oxidase derived from a strain of Humicola.

A preferred enzyme according to the invention is one which is stable at a pH of 5–10. In particular, the enzyme is one which has a pH optimum at a pH of about 5–9, such as about pH 7 using DCPIP or benzoquinones as the electron acceptor, about pH 7–9 using cytochrome C as the electron acceptor and about pH 9 using ferric cyanide as the electron acceptor. By way of comparison, the pH optimum of the previously described cellobiose oxidase from *M. thermophile* is 3–4 using ferric cyanide as the electron acceptor. A particularly preferred enzyme of the invention is one which has a temperature optimum of 55° C. at pH 9.5.

SDS-polyacrylamide gel electrophoresis (SDS-PAGE) with marker proteins and isolelectric focusing in a manner known to persons skilled in the art were used to determine the molecular weight and isoelectric point (pI), respectively. In this way, the molecular weight of a cellobiose oxidase of the invention was determined to be about 92 kD. The pI of the enzyme was determined to be about 4–5.

The enzyme of the invention may for instance be purified from a species of Humicola such as *Humicola insolens* e.g strain DSM 1800, deposited on 1 Oct. 1981 at the Deutsche Sammlung von Mikroorganismen, Mascheroder Weg 1B, D-3300 Braunschweig, FRG, in accordance with the provisions of the Budapest Treaty on the International Recognition of the Deposit of Microorganisms for the Purposes of Patent Procedure (the Budapest Treaty).

Another cellobiose oxidase which is active under alkaline conditions may be obtained from a strain of Sporormiella, such as *Sporormiella intermedia*, e.g. strain CBS 369.93, deposited on Jul. 1, 1993 at Centraalbureau voor Schimmelcultures, P.O. Box 273, 3740 AG Baarn, NL, in accordance with the provisions of the Budapest Treaty on the International Recognition of the Deposit of Microorganisms for the Purposes of Patent Procedure (the Budapest Treaty).

For industrial production of the cellobiose oxidase according to the invention, however, it is preferred to employ recombinant DNA techniques or other techniques involving adjustments of fermentations or mutation of the microorganisms involved to ensure overproduction of the desired enzymatic activities. Such methods and techniques are known in the art and may readily be carried out by persons skilled in the art.

The cellobiose oxidase may thus be one which is producible by a method comprising cultivating a host cell transformed with a recombinant DNA vector which carries a DNA sequence encoding said cellobiose oxidase or a precursor therefor, as well as DNA sequences encoding functions permitting the expression of the DNA sequence encoding the cellobiose oxidase or precursor therefor, in a culture medium under conditions permitting the expression of the cellobiose oxidase or precursor therefor and recovering the cellobiose oxidase from the culture.

A DNA fragment encoding the cellobiose oxidase or a precursor therefor may, for instance, be isolated by establishing a cDNA or genomic library of a cellobiose oxidase-producing microorganism, such as *Humicola insolens*, DSM 1800, and screening for positive clones by conventional procedures such as by hybridization to oligonucleotide probes synthesized on the basis of the full or partial amino acid sequence of the cellobiose oxidase, or by selecting for clones expressing the appropriate enzyme activity, or by selecting for clones producing a protein which is reactive with an antibody against a native cellobiose oxidase component.

Once selected, the DNA sequence may be inserted into a suitable replicable expression vector comprising appropriate promotor, operator and terminator sequences permitting the cellobiose oxidase to be expressed in a particular host organism, as well as an origin of replication enabling the vector to replicate in the host organism in question.

The resulting expression vector may then be transformed into a suitable host cell, such as a fungal cell, e.g. a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238,023 (of Novo Industri A/S), the contents of which are hereby incorporated by reference. The host cell may also be a yeast cell, e.g. a strain of *Saccharomyces cerevisiae*.

Alternatively, the host organisms may be a bacterium, in particular strains of Streptomyces and Bacillus, or *E. coli*. The transformation of bacterial cells may be performed according to conventional methods, e.g. as described in Sambrook et al., *Molecular Cloning: A Laboratory Manual*, Cold Spring Harbor, 1989.

The screening of appropriate DNA sequences and construction of vectors may also be carried out by standard procedures, cf. Sambrook et al., op. cit.

The medium used to cultivate the transformed host cells may be any conventional medium suitable for growing the host cells in question. The expressed cellobiose oxidase may conveniently be secreted into the culture medium and may be recovered thereform by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

By employing recombinant DNA techniques as indicated above, techniques of protein purification, techniques of fermentation and mutation or other techniques which are well known in the art, it is possible to provide a cellobiose oxidase of a high purity.

In another aspect, the present invention relates to an enzymatic agent comprising the cellobiose oxidase of the invention in the form of a non-dusting granulate, stabilized liquid or protected enzyme. Non-dusting granulates may be produced e.g. according to U.S. Pat. Nos. 4,106,991 and 4,661,452 (both to Novo Industri A/S) and may optionally be coated by methods known in the art. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

For use in a pulp bleaching process, it may be particularly advantageous to combine a cellobiose oxidase with another enzyme which has a complementary activity to that of the cellobiose oxidase, such as an endoglycanase and/or oxidoreductase (other than cellobiose oxidase). The endoglycanase may, for instance, be a hemicellulase such as a xylanase, mannanase or arabinase, or a cellulase such as an endoglucanase, in particular a xylanase the importance of which for lignin degradation has already been established. The xylanase is preferably one derivable from *Humicola insolens, Humicola lanuginosa, Bacillus pumilus, Malbranchea cinnamonea, Bacillus stearothermophilus, Thermonospora fusca, Streptomyces lividans* or *Streptomyces olivochromogenes*. In the process of degrading cellulose or other polysaccharide substrates, endoglycanases produce oligosaccharides, e.g. cellobiose and cellodextrins, which the cellobiose oxidase is able to use as substrates.

The oxidoreductase added to the enzymatic agent of the invention is preferably a peroxidase, such as a peroxidase producible by a strain of Coprinus, e.g. *Coprinus cinereus* or *Coprinus macrorhizus*, or a manganese peroxidase, a laccase (phenoloxidase), e.g. one producible by *Polyroros pensitus*, or a ligninase, e.g. one producible by a strain of Phanerochaete, e.g. *Phanerochaete chrysosporium*, or Trametes. The cellobiose oxidase is capable of generating substances acting as substrates for oxidoreductases, e.g. hydrogen peroxide.

The enzymatic agent according to the invention may additionally comprise a bleach accelerator such as a metal ion such as potassium ferric cyanide, a halide ion or an organic compound, such as a phenolic compound, e.g. 7-hydroxycoumarin, vanillin, p-hydroxycinnamic acid, 2,4-dichlorophenol, dichlorophenolindophenol, 3,5-tert.butyl-1, 2-benzoquinone, p-coumaric acid, anthraquinone or p-hydroxybenzene sulphonate. These compounds act as electron acceptors for the oxidation process.

In a further aspect, the present invention relates to a process of bleaching paper pulp comprising one or more enzymatic delignification steps, the process comprising treating pulp with a cellobiose oxidase. The enzymatic treatment will typically take place before chlorine bleaching of the pulp, and has the advantage that far lower amounts of chlorine are required to obtain a satisfactory brightness of the pulp than required in a conventional process not involving the use of enzymes.

The cellobiose oxidase is preferably one according to the invention, as this cellobiose oxidase is active at alkaline pH values. In this case, it will not be necessary to acidify the paper pulp before adding the enzyme.

In the process of the invention, the cellobiose oxidase is preferably used in combination with an endoglycanase, such as one of the endoglycanases suggested above, and/or an oxidoreductase such as one of the oxidoreductases indicated above. Such combination is expected to result in improved lignin degradation since, as indicated above, endoglycanases may provide substrates for cellobiose oxidases and they, in turn, may provide substrates for oxidoreductases, and consequently in an improved bleaching effect.

Thus, in a preferred embodiment of the process of the invention, the enzymatic treatment is carried out at a pH above about 7.

It is furthermore preferred that the enzymatic treatment is carried out at a temperature between 40° and 100° C., preferably between 40° and 80° C., more preferably between 50° and 70° C.

The enzymatic treatment is typically carried out for a period of 15 minutes to 24 hours, preferably between 30 minutes and 5 hours, more preferably between 30 minutes and 3 hours.

In the process of the invention, the consistency of the pulp is typically 5–35%, preferably 8–25%, more preferably 8–15%.

The process may further comprise extraction of lignocellulosic material with alkali after enzymatic treatment in each delignification step. After extraction, the lignocellulosic material is extensively washed with water. At least one conventional bleaching step may also be included in addition to enzymatic delignification.

The invention is further illustrated in the following example which is not in any way intended to limit the scope of the invention as claimed.

EXAMPLES

Example 1

Purification of Cellobiose Oxidase from *Humicola insolens*

A solution of Celluzyme™ (Novo Nordisk A/S) containing 21.4 g of protein was applied on a 300 ml arginine Sepharose column equilibrated with 50 mM Tris-HCl buffer, pH 7.0, and eluted with simultaneous gradients of Tris-HCl, pH 7.0–9.0, and 0–0.2M NaCl. The eluate containing the cellobiose oxidising activity was adjusted to pH 5.0 with HCl and applied on an S-Sepharose column in 20 mM Na-citrate pH 5. This column bound most of the cellulases while the cellobiose oxidase was eluted with the eluent. The pH of the eluate was adjusted to 7.0, and the eluate was applied on an anion exchange column (HPQ-Sepharose) previously equilibrated with 50 mM Tris-HCl pH 7.0. The column was eluted with a 0–1M NaCl gradient. This separated the minor cellobiose dehydrogenase (94 kDa and pI 4.4) from the major (92 kDa and pI of 4.0). Gel filtration on a Superdex 200 Hiload column eluted the cellobiose dehydrogenase with an apparent molecular weight of 92 kDa thus separating it from the contaminating cellulases of lower molecular weight.

SDS-PAGE and Electrofocusing

Analytical polyacrylamide gel electrophoresis of the different fractions was carried out on 10% gel slabs on a Bio-Rad apparatus according to the procedure recommended by the manufacturer with a Tris-glycine buffer system. Electrofocusing was carried out using a LKB multiphore apparatus and ampholine precast gels (LKB). Cellobiose oxidase activity after electrofocusing was determined using a 1% agarose overlayer containing cellobiose and DCPIP. The CBOs appeared as distinct clearing zones.

Biochemical Characterization

The amino acid composition was determined using an Applied Biosystems amino acid apparatus. The amino acid composition is shown in table 1. The values were calculated from the amino acid composition measured after 24 hours of hydrolysis. Tryptophan was determined according to the method of H. Edelhoch, *Biochemistry* 6, 1967, pp. 1948–1954.

The sample (250 pmole) was hydrolyzed with 1M HCl at 100° C. for 4 h. The acid was removed by vacuum evaporation and the identity of the sugars present was established by HPLC with a PAD detector (Dionex Corp. Sunnyvale, USA) and a Carbopak PAI microcolumn.

The protein is a glycoprotein with a total sugar content of 2% (w/w). The following sugars were detected: 4 mol of glucosamine, 4 mol mannose and 3 mol of galactose per mol enzyme.

TABLE 1

| Amino acid | CBO from *H. insolens* mol/mol | CBO from *M. thermophila*[a] mol/mol |
|---|---|---|
| Aspartate | 84 | 114 |
| Threonine | 75 | 66 |
| Serine | 57 | 54 |
| Glutamate | 79 | 54 |
| Proline | 41 | 54 |
| Glycine | 87 | 108 |
| Alanine | 62 | 75 |
| Cysteine | 2 | 9 |
| Valine | 35 | 60 |
| Methionine | 11 | 3 |
| Isoleucine | 23 | 36 |
| Leucine | 54 | 63 |
| Tyrosine | 23 | 30 |
| Phenylalanine | 25 | 36 |
| Lysine | 24 | 36 |
| Histidine | 8 | 12 |
| Arginine | 30 | 30 |
| Tryptophan | 49[b] | Not determined |

[a]Canevascini et al. (1991), Eur. J. Biochem. 198, 1991, pp. 43–52.
[b]Determined according to the method of H. Edelhoch, Biochemistry 6, 1967, pp. 1948–1954.

Identification of Prosthetic Groups

All absorption spectra and kinetic measurements were recorded on a Hewlet-Packard 8452A Diode Array Spectrophotometer in 0.75 ml black cuvettes with 1 cm optical path.

The fluorescence spectra were recorded on a PERKIN ELMER LS 50.

The spectrum of 500 μl 4.8 μM cellobiose oxidase was recorded and 10 μl of 5 mM cellobiose or a few grains of sodium dithionite (Merck) were added to give the reduced CBO. For the detection of the flavin group, fluorescence spectra of 1.7 μM cellobiose oxidase were recorded. Emission spectra for the exitation at 397 and 443 nm and exitation spectra for emission at 480 were recorded.

Extinction Coefficients

CBO $\epsilon_{280}=330,000 M^{-1} \cdot cm^{-1}$, the extinction coefficient was estimated using the amino acid composition and a molecular weight of 85 kDa.

Two extinction coefficients were measured for DCPIP: in the range pH 2 to 5.5 $\epsilon_{530}=7,500 M^{-1} \cdot cm^{-1}$ and from pH 5.5 to 10 $\epsilon_{600}=14,000 M^{-1} \cdot cm^{-1}$. Potassium ferricyanide (Merck): $\epsilon_{420}=970 M^{-1} \cdot cm^{-1}$, 3,5-di-tert-butyl-1,2-benzoquinone (Merck): $\epsilon_{410}=1,400 M^{-1} \cdot cm^{-1}$, Methylene Blue (Merck): $\epsilon_{610}=42,000 M^{-1} \cdot cm^{-1}$, cytochrome c (Sigma, from horse heart): $\epsilon_{550}=8,000 M^{-1} \cdot cm^{-1}$.

The visible spectrum of the cellobiose oxidase is characteristic of a hemoprotein. The oxidized state has an absorption maximum at 420 nm (γ band $203,000 M^{-1} \cdot cm^{-1}$) while the spectra of the reduced state show absorption peaks at 564 nm (α band, $61,000 M^{-1} \cdot cm^{-1}$), 534 nm (β band, $46,000 M^{-1} \cdot cm^{-1}$) and 432 nm (γ band, $287,000 M^{-1} \cdot cm^{-1}$) which is typical of a cytochrome b (cf. G. Canevascini et al., Eur. J. Biochem. 198, 1991, p. 43). The flavin group was weakly fluorescent, with an emission maximum at 480 nm and exitation maxima at 397 and 443 nm.

Determination of Activity

The measurements were performed in 0.1M sodium phosphate buffer at pH 7.5 at 40° C. 450 μl of a mixture of 100 μM of 2,6-Dichlorophenol-indophenol (DCPIP, Merck), 250 μM of cellobiose (Sigma) were mixed with 50 μl enzyme. Units of activity equals μmol cellobiose oxidized (DCPIP reduced) per min.

Catalytic Properties

Identification of Oxidation Product 40 mg of cellobiose was mixed with 30 mg of DCPIP in 10 ml water and 100 μl of 1.6 μM cellobiose oxidase was added. The mixture was stirred overnight at room temperature. The mixture was diluted with water and extracted several times with ethyl acetate to remove the reduced and non-reduced DCPIP. $^1H$ NMR and $^{13}C$ NMR spectra of cellobiose and the oxidized product in $D_2O$ were then taken on a Bruker ACP 300 spectrometer. Cellobiose: $^1H$ NMR ($D_2O$): δ (ppm) 4.65 (β, H-1, $J_{1,2}$=8.0 Hz), 5.21 (α,H-1,$J_{1,2}$=3.7 HZ) (Claeyssens et al., 1990); $_{13}C$ NMR ($D_2O$): δ (ppm) 92.9 (α,C-1), 96.8 (β,C-1) (Dorman and Roberts, 1971). Cellobionolactone: $^1H$ NMR ($D_2O$): no peaks between 4.28 ppm and 4.75 ppm (H-1', $J_{1',2'}$=8.0 HZ); $^{13}C$ NMR ($D_2O$): δ (ppm) no peaks between 84.2 ppm (C-4) and 105.5 ppm (C-1').

All measurements were performed in 0.1M sodium phosphate buffer, pH 7.5, at 40° C. 450 μl of 15 μM to 5 mM (depending on $K_m$) of electron donors and acceptors and 50 μg of 70 nM to 200 nM of enzyme depending on $k_{cat}$ were mixed to a total volume of 500 μl. The reactions were monitored for 400 s as changes in absorbance at the appropriate wavelength (see above). The benzoquinone was dissolved in ethanol to a concentration of 10 mM and diluted in phosphate buffer to the appropriate concentration. The catalytic constants ($k_{cat}$) were expressed as mol of oxidized cellobiose/s/mol of enzyme. One equivalent of DCPIP, Methylene Blue or benzoquinone oxidizes one equivalent of cellobiose whereas two equivalents of cytochrome c or ferricyanide oxidizes one equivalent of cellobiose. The kinetic constants were determined using Lineweaver-Burke plots and were the result of dual determinations.

The enzyme was found to be able to oxidize different disaccharides and cellodextrins as listed in table 2. It was not able to oxidize glucose. The product of the oxidation of cellobiose was identified using $^1H$ and $^{13}C$ NMR in $D_2O$. In both spectra the peaks corresponding to the α- and β-anomer of the reducing end had disappeared implying oxidation at C-1 resulting in cellobionic acid.

Cellobiose and the cellodextrins are readily oxidized by the cellobiose oxidase with approximately the same $k_{cat}$ and $K_m$ independent of the degree of polymerization as seen in table 2. Lactose is oxidized at a rate comparable to those of the cellodextrins. Maltose and xylobiose are also substrates. However, these substrates display a significantly weaker binding than that of the cellodextrins. Glucose, N,N-Diacetylchitobiose and N-Acetyllactosamine are not oxidized.

TABLE 2

| Electron donor Sugar + 90 μM DCPIP | $K_m$ (μM) | $k_{cat}$ (s$^{-1}$) |
|---|---|---|
| Cellobiose | 11 | 10 |
| Cellotriose | 19 | 8.5 |
| Cellotetraose | 21 | 8.5 |
| Cellopentaose | 17 | 8.3 |
| Lactose | 51 | 10 |
| Maltose | 11,000 | 0.83 |
| Xylobiose | 7,100 | 2.15 |
| N,N-Diacetyl-chitobiose | — | 0 |
| N-Acetyllactosamine | — | 0 |
| Glucose | — | 0 |

TABLE 3

| Electron acceptor + 225 μM cellobiose | $k_m$ (μM) | $k_{cat}$ (s$^{-1}$) |
|---|---|---|
| DCPIP | 26 | 12 |
| Methylene Blue | 18 | 1.85 |
| Benzoquinone | 132 | 15 |
| Ferricyanide | 12 | 10 |
| Cytochrome c | 93 | 19 |

Determination of Temperature Activity at Alkaline pH

For temperature activity the measurement was performed in 0.1M glycine buffer at pH 9.5 at different temperatures, using 550 μM cytochrome C (Sigma from horse heart), 225 μM cellobiose (Sigma) and enzyme mixed in a total volume of 500 μl. The activity was measured as reduction of cytochrome C using a molar extinction coefficient of 8,000 $M^{-1} \cdot cm^{-1}$. Optimal activity was found at 55° C. during 5 minutes incubation. The result appears from FIG. 1.

Figure 2:
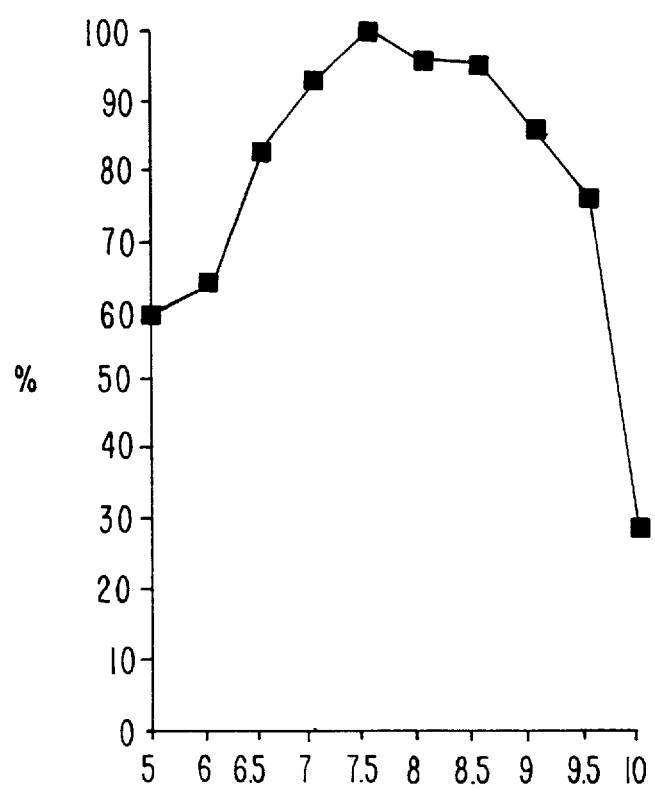
FIG. 2 is a plot of relative activity of the cellobiose oxidase enzyme versus pH.

The pH activity profile was measured at 40° C. activity using sodiumacetate buffer from pH 3.5 to 6.5, sodium phosphate from pH 6.5 to 8.5 and glycine buffer from pH 9 to 10. All buffers at 0.1M concentration and the enzyme and cellobiose and cytochrome c concentration as above. Optimum activity was obtained at pH 7.5 and 75% residual activity was obtained at pH 9.5. The steady state kinetic was followed for 10 min. The result appears from FIG. 2.

Coupled Assay for Cellulases

The ability of the cellobiose oxidase to oxidize cellodextrins by means of an electron acceptor was utilized in an assay for cellulases. By using a substrate without a reducing end, such as a reduced cellodextrin, the reducing ends formed by the hydrolysis by the cellulase will be oxidized by the CBO. Simultaneously the coloured electron acceptor, dichlorophenolindophenol (DCPIP), is reduced by cellobiose oxidase to a colourless compound making it possible to follow the reaction spectrophotometrically at 600 nm DCPIP was chosen as electron acceptor because of its high extinction coefficient.

With this assay the kinetic constants for reduced cellodextrins of 5 different cellulases have been determined (table 2). The results show the applicability of this coupled system. The enzymes show very different substrate specificity, some of them requiring quite long substrates making it impossible to use the umbelliferyl cellobiosides and lactosides available for steady state kinetic. In conclusion it is made possible with the assay to measure steady state kinetics for a wide range of cellulases which is a good tool in the further understanding of the mechanism of the cellulases.

The inhibitors methyl 4-thiocellotrioside, methyl 4-thiocellotetraoside and methyl 4-thiocellopentaoside were synthesized at the laboratory in Grenoble[5]. The inhibition constants were determined for two cellulases using the developed assay. The results are presented in table 3.

| Enzymes | Constants | S-DP3 | S-DP4 | S-DP5 |
|---|---|---|---|---|
| CBH II | $K_L$ ($\mu$M) | 1,400 | 270 | 15 |
| Endo A | $K_L$ ($\mu$M) | 300 | 75 | 35 |
|  | $K_{LS}$ ($\mu$M) | 2,000 | 1,000 | — |

1 $\mu$mole Chlorogenic acid
1 unit of Coprinus cinereus peroxidase (1 PODU)*
0.4 $\mu$mole hydrogenperoxide
150 units of Cellobiose oxidase in 2 ml 0.1M phosphate buffer, pH 7. The temperature was room temperature.

*PODU is described in Novo Nordisk analytical method AF 310/1, available on request from Novo Nordisk A/S, Novo Allé, 2880 Bagsvaerd, Denmark.

The reaction was followed by UV-absorbance at 440 nm at which wavelength the formation of quinones can be detected. Due to the action of peroxidase the absorbance increased corresponding to the formation of quinones. After 80 seconds 15 $\mu$mole of cellobiose was added. The absorbance immediately started to decrease as a result of the reduction of quinones catalyzed by cellobiose oxidase.

In a similar experiment chlorogenic acid was replaced by lignosulfonate (4 mg). The results were the same: initially $A_{440}$ increased due to formation of quinones but as soon as cellobiose was added, the absorbance decreased.

In both cases the absorbance levelled out after app. 4 minutes at a level similar to the initial level, i.e. quantitative reduction of the quinones was obtained.

Example 3

Delignification of Pulp

Delignification of pulp was examined using a Scandinavian pine Kraft pulp. The following samples were prepared:

a) 2–5 dry pulp
   10 units
   15 $\mu$mole hydrogen peroxide
   150 $\mu$mole cellobiose
   6000 units of cellobiose oxidase
   70 ml 0.1M phosphate buffer, pH 8 b) as a) except that no cellobiose oxidase was added.

The samples were incubated in a shaking water bath at 40° C. for 24 hours. After filtration the pulp samples were washed with water and dried. As an indicator of the degree of delignification kappa numbers were determined, according to TAPPI standards:

|  | Red. DP3 | | | Red. DP4 | | | Red. DP5 | | | Red. DP6 | | |
|---|---|---|---|---|---|---|---|---|---|---|---|---|
| Enzymes | Km ($\mu$M) | $k_{cat}$ (s$^{-1}$) | Enzym conc. (nM) | Km ($\mu$M) | $k_{cat}$ (s$^{-1}$) | Enzym conc. (nM) | Km ($\mu$M) | $k_{cat}$ (s$^{-1}$) | Enzym conc. (nM) | Km ($\mu$M) | $k_{cat}$ (s$^{-1}$) | Enzym conc. (nM) |
| Endo A | 500 | 0.24 | 940 | 26 | 29 | 1.7 | 14 | 40 | 1.7 | — | — | — |
| CBH II | — | 0 | — | 490 | 0.14 | 750 | 3.0 | 0.75 | 59 | 4.7 | 0.94 | 59 |
| Endo B | — | 0 | — | 1,500 | 0.84 | 250 | 150 | 0.86 | 50 | 52 | 14 | 6.3 |
| EG A | — | 0 | — | — | 0 | — | 460 | 0.00 | 1,400 | 54 | 0.15 | 290 |
| EG C | — | 0 | — | 1,600 | 0.43 | 390 | 68 | 13 | 7.8 | 71 | 11 | 5.2 |

Example 2

Lignin Degradation

Lignin degradation by reduction of quinones formed by the action of oxidoreductases was examined using cellobiose oxidase in combination with peroxidase. First a lignin model compound, chlorogenic acid, was applied.

The reaction mixture consisted of:

| Sample | a | b |
|---|---|---|
| Kappa number | 23.31 | 26.33 |

Thus, a significant delignification could be obtained upon treatment of pulp with cellobiose oxidase and peroxidase.

Example 4

Production of *Sporormiella intermedia* cellobiose oxidase 100 ml twice concentrated YM medium (containing 1% glucose, 0.5% peptone, 0.3% malt extract and 0.3% yeast extract, pH 6.5) in a 500 ml Erlenmeyer shake flask provided with two baffles was inoculated with a culture of *Sporormiella intermedia,* strain CBS 369.93 in PDA agar. Cultivation was carried out at 28° C. and 220 rpm. Aliquots of the culture supernatant (25 µl) were taken at intervals and assayed for cellobiose oxidase activity in microtiter plates containing 50 µl of 250 mM potassium phosphate buffer, pH 6.5, 50 µl of 100 mM cellobiose and 25 µl of 0.4 mM 2,6-dichlorophenolindophenol. Cellobiose activity was determined as decolouration of 2,6-dichlorophenolindophenol.

We claim:

1. An isolated enzyme exhibiting cellobiose oxidase activity, wherein the enzyme is obtained from Humicola and has a relative activity of at least 70% at a pH of about 9 and a temperature of about 50° C.

2. The enzyme according to claim 1, wherein the enzyme is obtained from *Humicola insolens* strain DSM 1800.

3. The enzyme according to claim 1, which has a molecular weight of about 92 kD when determined by SDS-PAGE.

4. The enzyme according to claim 1, which retains about 30–100% of maximum activity at a pH of 5–10.

5. The enzyme according to claim 4, which has a pH optimum at pH 5–9.

6. The enzyme according to claim 1, which has a pI of about 4–5.

7. An enzymatic agent comprising cellobiose oxidase according to claim 1 in the form of a nondusting granulate, stabilised liquid, or protected enzyme.

* * * * *

UNITED STATES PATENT AND TRADEMARK OFFICE
CERTIFICATE OF CORRECTION

PATENT NO. : 5,866,392

DATED : February 2, 1999

INVENTOR(S) : Schou et al.

It is certified that error appears in the above-identified patent and that said Letters Patent is hereby corrected as shown below:

Col. 1, line 60, delete "guinones" and insert --quinones--.

Col. 2, line 58, delete "isolelectric" and insert --isoelectric--.

Col. 4, line 8, delete "thereform" and insert --therefrom--.

Col. 4, line 55, delete "Polyroros" and insert --Polyporos--.

Signed and Sealed this

Twenty-eighth Day of December, 1999

Attest:

Q. TODD DICKINSON

*Attesting Officer*     *Acting Commissioner of Patents and Trademarks*